United States Patent [19]

Tsunoo et al.

[11] Patent Number: 5,256,412
[45] Date of Patent: Oct. 26, 1993

[54] ANTI-HIV AGENT

[75] Inventors: Hajime Tsunoo; Masao Takami; Kenji Mizumoto, all of Odawara, Japan

[73] Assignee: Meiji Milk Products Co., Ltd., Tokyo, Japan

[21] Appl. No.: 930,349

[22] Filed: Aug. 17, 1992

Related U.S. Application Data

[62] Division of Ser. No. 576,439, Sep. 10, 1990, Pat. No. 5,164,486.

[30] Foreign Application Priority Data

Jan. 9, 1989 [JP] Japan ................................. 1-2574
Jan. 27, 1989 [JP] Japan ................................. 1-18790

[51] Int. Cl.$^5$ ............................................... A61K 37/02
[52] U.S. Cl. ................................... 424/85.8; 530/362; 530/363; 530/382; 530/387.1; 530/394
[58] Field of Search ............... 530/363, 362, 382, 387, 530/394, 410, 387.1, 394; 424/85.8

[56] References Cited

FOREIGN PATENT DOCUMENTS 0038667 10/1981 European Pat. Off. .
1212844 11/1970 United Kingdom .

OTHER PUBLICATIONS

Jonas et al. Biochemistry vol. 9, No. 24, (1970) pp. 4729-4735.
Butler et al. Method Enzymol., 25, (1972) pp. 191-199.

Primary Examiner—Michael G. Wityshyn
Assistant Examiner—Choon Koh
Attorney, Agent, or Firm—Oblon, Spivak, McClelland, Maier & Neustadt

[57] ABSTRACT

The invention relates to an anti-HIV agent comprising as an effective component a plasma protein of which the polarity of the amino group of the amino acid residue constituting the plasma protein is chemically modified into a negative moiety by a carboxylic acid, for example, by maleic anhydride or succinic anhydride. Plasma proteins modified with dicarboxylic anhydride, which are the effective components of the anti-HIV agent of this invention, inhibit the formation of large cells in mixed culturing of HIV infected cells and non-infected cells as well as the direct infection of helper T cells with HIV. They are very safe compounds and are expected to be applicable to the treatment of HIV infected patients 4 Claims, 9 Drawing Sheets

ANTI-HIV AGENT

This is a division of application Ser. No. 07/576,439, filed on Sept. 10, 1990, U.S. Pat. No. 5,164,486.

FIELD OF INDUSTRIAL APPLICATION

This invention relates to a novel anti-HIV (human immunodeficiency virus) agent.

BACKGROUND OF THE INVENTION

Extensive molecular-biological and biochemical studies have been undertaken on HIV, since the virus, the HIV, has been uncovered as a cause of acquired immunodeficiency syndrome (hereinafter referred to as "AIDS"). These studies have been successful in gradually unveiling the virus itself, as well as the mechanism of the cell infection with the virus. Two routes through which the cells are infected with the virus reported; a route by which HIV released into blood directly combines with the target T-cells and a route in which cells infected with HIV combines with uninfected cells to form a large cells [Weber, J. N. and Rice, R. A. *Scientific American* (Japanese version), 18, No. 12, 88–95 (1988)]. At the present, however, almost all AIDS patients die because of the lack of an effective AIDS cure. Studies are ongoing all over the world for discovering anti-HIV agents which are effective for the treatment of AIDS patients infected with HIV.

Only 3'-azido-2',3'-dideoxy-thymidine (hereinafter abbreviated as AZT) has been so far sold on the market as an anti-HIV agent [Mitsuya, H. et al. *Proc. Natl. Acad. Sci.* USA, 82, 7096–7100 (1985)]. AZT, however, remarkably inhibits bone marrow cell growth, as a side effect, and thus is problematic for long-term administration [Richmann, D. D. et al., *New Eng. J. Med.*, 317, 185–191 (1987)].

AZT is a derivative of 2',3'-dideoxynucleoside. Known at the present as an anti-HIV compound having a similar structure is 2',3'-dideoxycytidine. This compound is under investigation at the clinical stage. Pyrymidine nucleoside derivatives (Japanese Patent Laid-open No. 107924/1988) and puryne nucleoside derivatives (Japanese Patent Laid-open No. 107936/1988) are other compounds which are the derivatives of 2',3'-dideoxynucleoside.

Besides the above-mentioned compounds, soluble CD4 and dextran sulfate are considered to be promising anti-HIV agent candidates and clinical tests are ongoing on these compounds. CD4 is a glycoprotein which is abundantly present, especially on the surface of helper T cells, a major target of HIV. Helper T cells are infected with HIV through strong bonding of CD4 with a glycoprotein called gp120 which exists on the surface of HIV particles. If a soluble CD4 is administered to a patient, gp120 is occupied by this extraneous CD4. This prevents the HIV from bonding with the CD4 existing on the surface of helper T cells, thus prohibiting the infection of helper T cells with HIV.

Dextran sulfate has conventionally been used as a blood coagulation inhibitor or as a cholesterol depressor. The compound has drawn much attention since the discovery of the effect to inhibit infection or replication of HIV [*Jpn. J. Cancer Res.* 78, 1164–1168 (1987)]. Dextran sulfate, however, brings about a side effect of causing liver disorders. In addition, the blood coagulation inhibiting capability possessed by dextran sulfate makes it impossible to administer this compound to hemophiliac AIDS patients.

MEANS FOR THE SOLUTION OF THE PROBLEMS

The present inventors have carried out extensive studies on the development of a compound useful as an anti-HIV agent. As a result, the inventors have found that if the amino group on the plasma protein-constituting amino acid residue is chemically modified to convert its polarity from positive into negative, the chemically modified plasma protein inhibits HIV-infected cells and HIV-uninfected cells from fusing together and thus from growing into large cells resulting in denaturing or death of the cells, and yet such a chemically modified plasma protein exhibits the least in vivo and in vitro toxicity. That is, the present inventors have found that said chemically modified plasma protein could be used as an excellent anti-HIV agent.

Disclosure of the Invention

The present invention is to provide an anti-HIV agent comprising as an effective component a protein of which the polarity of the amino group of the amino acid residue constituting the plasma protein is chemically modified into a negative moiety.

BRIEF DESCRIPTION OF THE DRAWINGS

FIG. 2(A) is a sketch of cells in a culture broth wherein Molt-4 clone no. 8 alone was cultured. FIG. 2(B) is a sketch of cells in a culture broth wherein Molt-4/HIV and Molt-4 clone no. 8 were cultured in a mixture without the addition of a test sample. FIG. 2(C) is a sketch of cells in a culture broth wherein Molt-4/HIV and Molt-4 clone no. 8 were cultured in a mixture with an addition of 20 $\mu$g/ml of M-HSA of the present invention. FIG. 2(D) is a sketch of cells in a culture broth wherein Molt-4/HIV and Molt-4 clone no. 8 were cultured in a mixture with an addition of 50 $\mu$g/ml of DS.

FIG. 6(A) represents a sketch of cells in a culture broth wherein Molt-4 clone no. 8 alone was cultured. FIG. 6(B) is a sketch of cells in a culture broth wherein Molt-4 clone no. 8 was cultured with the addition of a solution containing only HIV. FIG. 6(C) is a sketch of cells in a culture broth wherein Molt-4 clone no. 8 was cultured with the addition of a solution containing HIV and 100 μg/ml of M-HSA of the present invention. FIG. 6(D) is a sketch of cells in a culture broth wherein Molt-4 clone no. 8 was cultured with the addition of a solution containing HIV and 300 μg/ml of M-Tf of the present invention.

BEST MODE FOR CARRYING OUT THE INVENTION

Figure 1:
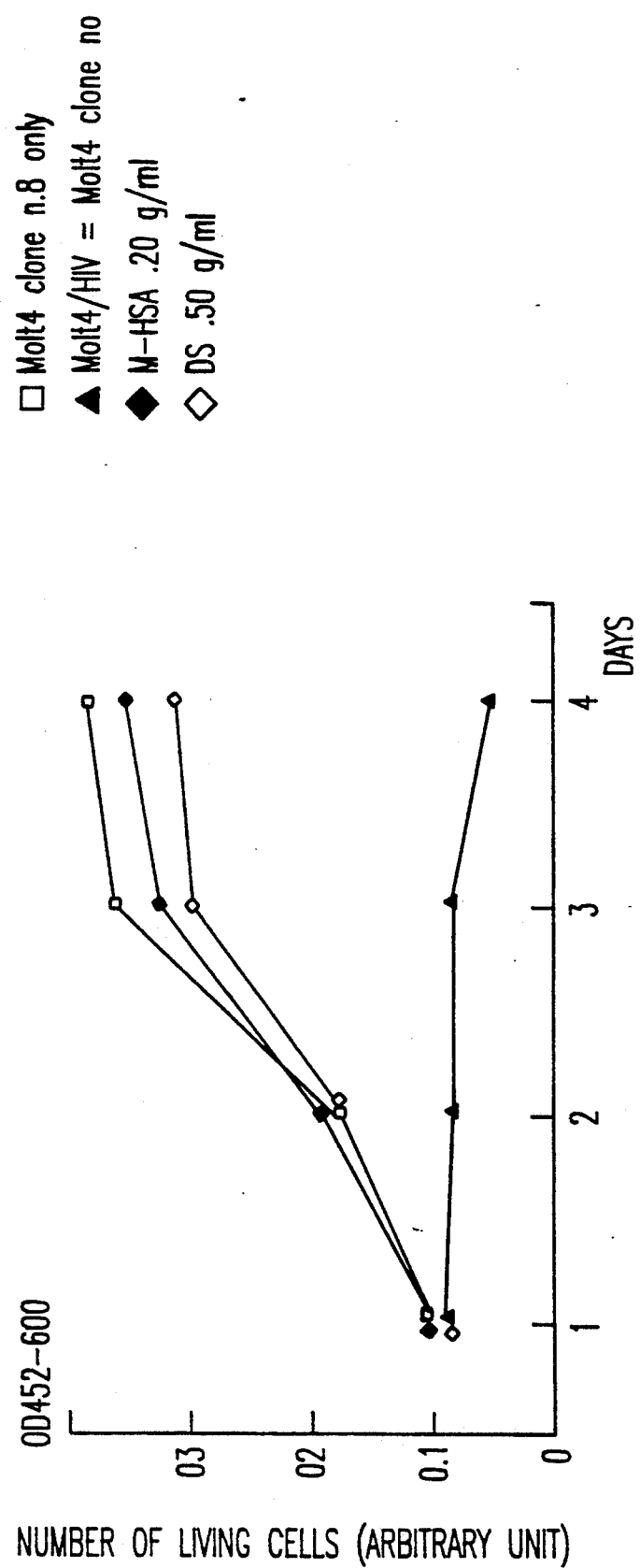
FIG. 1 is a graph showing the number of living cells over time counted by means of the MTT assay in a mixed culture system to which M-HSA or DS was added to a mixed culture system of Molt-4/HIV and Molt-4 clone no. 8 to a final concentration of 20 $\mu$g/ml (M-HSA) or 50 $\mu$g/ml (DS) to investigate the effect of M-HSA or DS to inhibit denaturing or death of cells due to large cell formation.
Figure 2A:
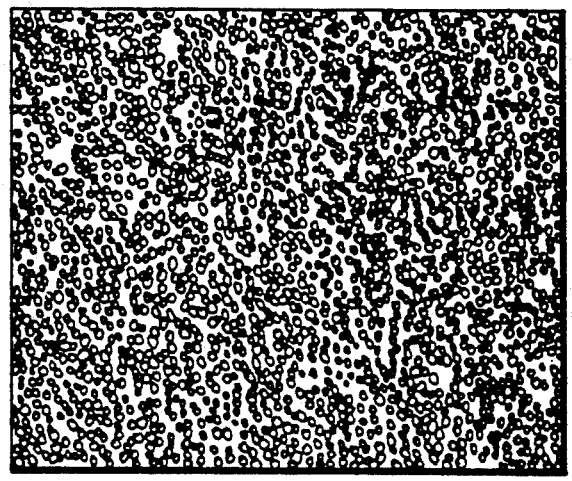
FIGS. 2(A) to 2(D) are sketches of the cell morphology in culture systems of Molt-4/HIV and Molt-4 clone no. 8 observed by microscopy on the fourth day of the culturing.
Figure 2B:
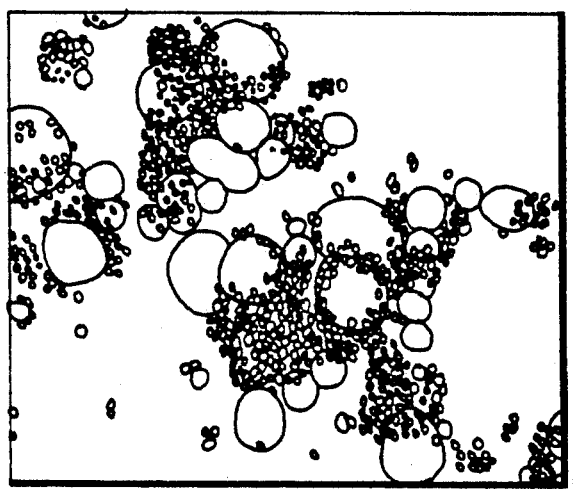
Figure 2C:
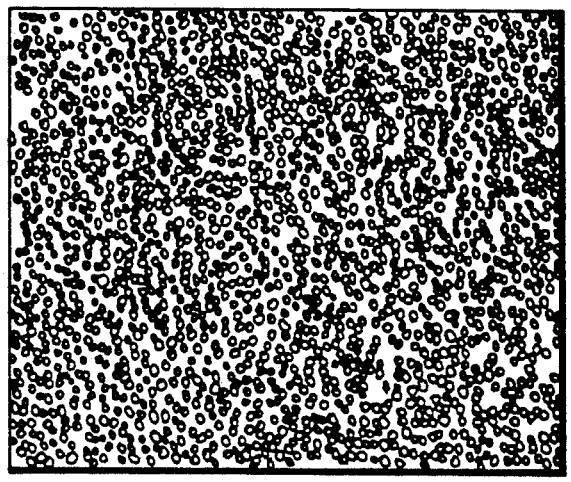
Figure 2D:

Plasma protein derived from human being, such as human serum albumin, human immunoglobulin, human transferrin, and human fibrinogen, are considered to be desirable from the aspect of antigenicity. Beside these proteins, calf plasma proteins can be used as a plasma protein which is to be chemically modified in the present invention.

Dicarboxylic anhydrides, preferably maleic anhydride, succinic anhydride, and the like, can be given as chemicals which convert the amino group of the constituent amino acid residue from positive into negative.

Since the purpose of the chemical modification is to obtain a plasma protein having an HIV activity, the chemical modification can be carried out by reacting said plasma protein and said chemicals for the modification in a weak alkaline solution around room temperature, and any conditions can be employed so long as the amino group of the amino acid residue constituting the plasma protein can be carboxylated, e.g. by maleyl- or succinyl-modification, and its electric charge is converted from positive to negative. There are no strict limitations as to the number and the primary structural site of the amino acid to be modified. It should be understood that even if a part of functional groups other than amino group in the side chain are chemically modified as a result of a side reaction, such a chemically modified plasma protein falls within the scope of the present invention so long as the resulting product possesses an anti-HIV activity. When carboxylic anhydride is used, the modified site has a structure represented by $-NHCORCOO^-$, wherein R represents an organic group.

Preferable embodiments of the present invention are described in more detail.

Illustrating the methods for preparing the chemically modified plasma protein of this invention, one example of maleyl-modification has been proposed by Butler, P. J. G. and Hartley, B. S. [*Method Enzymol.*, 25, 191-199 (1972)] and a succinyl-modification method has been proposed by Habeeb, A. F. S. A. et al. [*Biochim. Biophys. Acta,* 29, 587 (1958)]. Specifically, a maleyl-modified plasma protein can be prepared by the treatment of a plasma protein with maleic anhydride in a weakly alkaline solution, and a succinyl-modified plasma protein can be prepared by the treatment of a plasma protein with succinic anhydride in a weakly alkaline solution.

Maleyl- or succinyl-modified plasma proteins remarkably inhibit formation of large cells by the bonding of HIV which is released into the blood to the target cells and by the fusion of HIV-infected cells with uninfected cells.

A dose to be administered of maleyl- or succinyl-modified plasma protein which is the effective component of the anti-HIV agent of this invention varies depending on the degree of the symptoms, the age, the sex, and the ability of the subject to accept such a chemically modified plasma protein. For adult patient, the dose is generally 10 μg to 10 g per day, and this dosage may be administered at one time or over several administrations each day. The anti-HIV agent of this invention may be either administered individually or used together with one or more other anti-HIV agents.

Intravenous injection is usually applied as the method of administration.

The injection liquid can be prepared according to a conventional method using, as required, commonly known carriers or adjuvants such as pH buffers, solubilizers, preservatives, stabilizers, and the like.

Preparation of the chemically modified plasma protein of this invention is illustrated by way of example with respect to maleyl-modified human serum albumin.

<Preparation Example>

The method proposed by Butler et al. [Butler, P. J. G. and Hartley, B. S.; *Method Enzymol.,* 25, 191-199 (1972)] was employed.

300 mg of human serum albumin (No. A 8763 produced by Sigma Co.) was dissolved into 30 ml of 0.2 M $Na_2B_4O_7$ solution which was adjusted to pH 8.5 with hydrochloric acid. Maleic anhydride powder was added to 30 ml of this solution to a final concentration of 0.1M, while adding $Na_2CO_3$ powder to maintain the pH of the solution at 8.5 or greater. All of these procedures were performed at room temperature. The reaction product was thoroughly dialyzed at 4° C. twice with 3 liters of 0.1M $NaHCO_3$, once with 3 liters of purified water, then twice with 3 liters of 0.01M $NH_4HCO_3$.

After the dialysis, the dialyzed internal solution was lyophilyzed using a lyophilyzer (Space Seva Delux 75035, manufactured by Labconca Co.) to produce the target sample of maleyl-modified human serum albumin (hereinafter referred to as M-HSA) in a powdery form.

Characteristics of M-HSA thus produced were as follows:

(1) Molecular Weight

The molecular weight of the final M-HSA product measured by 8% SDS-polyacryl amide gel electrophoresis was 66,000.

(2) Solubility

Soluble into water.

(3) UV Absorptivity

The substance exhibited a greater UV absorbance in the neighborhood of 250 nm than non-modified human serum albumin (hereinafter referred to as HSA).

The maleyl-modification degree of M-HSA was found to be 90% by the calculation from the amount of the non-modified amino group using untreated HSA as a control. The method of Fields [Fields, R.; *Methods Enzymol.*, 25, 464–468 (1972)] was employed for the measurement of the amount of the amino group.

EXAMPLES

The present invention is hereinafter described by way of examples. All of the examples below are based upon in vitro systems using cultured cells, since in vivo experiments using an anti-HIV agent was difficult because of the absence of suitable animals which are infected by HIV.

Types of cells, the method of assay, the reagents, and the method of evaluation of the anti-HIV effects of various chemically modified plasma proteins used in the examples, are first explained.

Cell strains used in Examples 1–3 were human acute leukemia cells Molt-4. They included HIV infected cells Molt-4/HIV [Yamamoto, N. et al.; *Int. J. Cancer*, 36, 445–451 (1985)] and Molt-4 clone no. 8 which is highly susceptible to HIV [Yamamoto, N. et al.; *J. Virol.*, 57, 1159–1162 (1986)]. These cell strains were provided by Dr. Naoki Yamamoto of the Medical Department of Yamaguchi University.

The culture liquid used was 10% (v/v) bovine fetus serum solution of RPMI-1640 ("culture liquid" is also referred to as "culture medium" from time to time in this specification).

Normal cell culture conditions (Air:$CO_2$=95:5, temperature: 37° C.) were employed for culturing the cells.

The number of living cells in a culture mix of Molt-4/HIV and Molt-4 clone no. 8 was measured according to the MTT [3-(4,5-dimethylthiazol-2-yl)-2,5-diphenyl tetrazolium bromide] assay ["Immunological Experimental Procedure XIII" (edited by Japan Immunology Association), pp 4477–4482] or the Trypan blue color exclusion method. The number of living cells in a direct infection system of Molt-4 clone no. 8 with HIV was also measured by the same method.

The number of living cells by the Trypan blue color exclusion method was calculated as follows. A Trypan blue-physiological saline mixed solution was prepared by mixing 4 volumes of 0.2% Trypan blue solution and 1 volume of 5-fold physiological saline water. Then, an equal volume of the Trypan blue-physiological saline mixed solution and the cell suspension used in Examples were mixed, and the number of cells not stained with the pigment was counted using a blood cell counter.

Human serum albumin (No. A 8763), human immunoglobulin G (No. G 4386), human transferrin (No. T 0519), human fibrinogen (No. F 3879), and bovine serum albumin (No. A 7638) used were those supplied by Sigma Chemical Co. The numbers in the parentheses indicate the Sigma product numbers. In addition, dextran sulfate (No. D 0768; average molecular weight: 5,000, manufactured by Sigma) was used as a known anti-HIV agent for comparison.

Activities of chemically modified plasma proteins and dextran sulfate (hereinafter referred to as "test sample" or "medicine") were evaluated by means of the inhibitive ratio (hereinafter referred to as "IR") achieved by the samples of the cell-denaturing or cell-death caused by large cell formation. Here, IR is defined by the following equation:

$$IR = \frac{A - B}{C - B} \times 100 \; (\%)$$

wherein A is the value measured by the MTT assay or the Trypan blue color exclusion method on the Molt-4/HIV -Molt-4 clone no. 8 mixed culture system to which a test sample was added; B is the value measured by the MTT assay or the Trypan blue color exclusion method on the Molt-4/HIV-Molt-4 clone no. 8 mixed culture system to which no medicine was added; and C indicates the value measured by the MTT assay or the Trypan blue color exclusion method on the independent culture of Molt-4 clone no. 8.

EXAMPLE 1

(Chemically modified albumin inhibitive effect on large cell formation in a mixed HIV infected cell-HIV non-infected cell culture system)

Mixed culturing of Molt-4/HIV and Molt-4 clone no. 8 cells is known to result in rapid production of multi-nuclear large cells, followed by the death of the multi-nuclear large cells [Yamamoto, N. et al.; *J. Virol.*, 57, 1159–1162 (1986)]. An experiment was performed to confirm the activity of M-HSA and succinyl-modified serum albumin (hereinafter referred to as "S-HSA") to inhibit this phenomenon.

Samples used were M-HSA, S-HSA, and maleyl-modified bovine serum albumin (hereinafter referred to as "M-BSA"). In addition, non-modified HSA was used as a control and dextran (hereinafter referred to as "DS") was used as a representative sample from known anti-HIV agents. These samples were added to produce various concentrations to Molt-4/-HIV-Molt-4 clone no. 8 mixed culture systems to observe the inhibitory effect of the samples.

A 96- or 24-hole microplate was used for the mixed culturing of cell strains Molt-4/HIV and Molt-4 clone no. 8. The culture was carried out for each strain at a concentration of $0.5 \times 10^5$/ml and $2.0 \times 10^5$/ml. As controls a system to which no anti-HIV agent was added and a system containing only Molt-4 clone no. 8 cells were cultured.

In the course of the cell culturing, the effects of anti-HIV agents inhibiting cell-denaturing and -death caused by large cell formation were measured by the MTT assay over time. The cell morphology was observed with a microscope The results are shown in FIGS. 1, 2-(A) to 2-(D), 3, and 4.

FIG. 1 shows the effect of M-HSA or DS inhibiting denaturing or death caused by large cell formation over time in a mixed culture system to which M-HSA or DS was added to a final concentration of 20 μg/ml (M-HSA) or 50 μg/ml (DS). Living cells were counted by means of the MTT assay. In the figure, the line connecting open squares represents the number of living cells in the culture broth containing only Molt-4 clone no. 8 cell strain, the line connecting solid triangles represents those in the culture broth to which neither M-HSA nor DS was added, the line connecting solid rhomboids represents those in the culture broth to which 20 μg/ml of M-HSA was added, and the line connecting open rhomboids represents those in the broth to which 50 μg/ml of DS was added. The IR for M-HSA was 86% on the third day and 88% on the fourth day, and the IR for DS was 76% and 78% on the third and fourth days respectively.

FIGS. 2(A) to 2(D) are sketches of the cell morphology observed by microscopy on the fourth day of the culturing. As clear from these sketches, a large, agglomerated cells which were denatured and died were observed in the mixed culture system of strains Molt-4/HIV and Molt-4 clone no. 8 [FIG. 2(B)], whereas the cells in the broth in which only Molt-4 clone no. 8 cell strain was cultured were alive [FIG. 2(A)]. In contrast, the large cell denaturing or death inhibiting effect was observed in the culture broth to which 20 μg/ml of M-HSA was added [FIG. 2(C)]. A similar effect was also recognized in the culture broth to which 50 μg/ml of DS was added [FIG. 2(D)].

Figure 3:
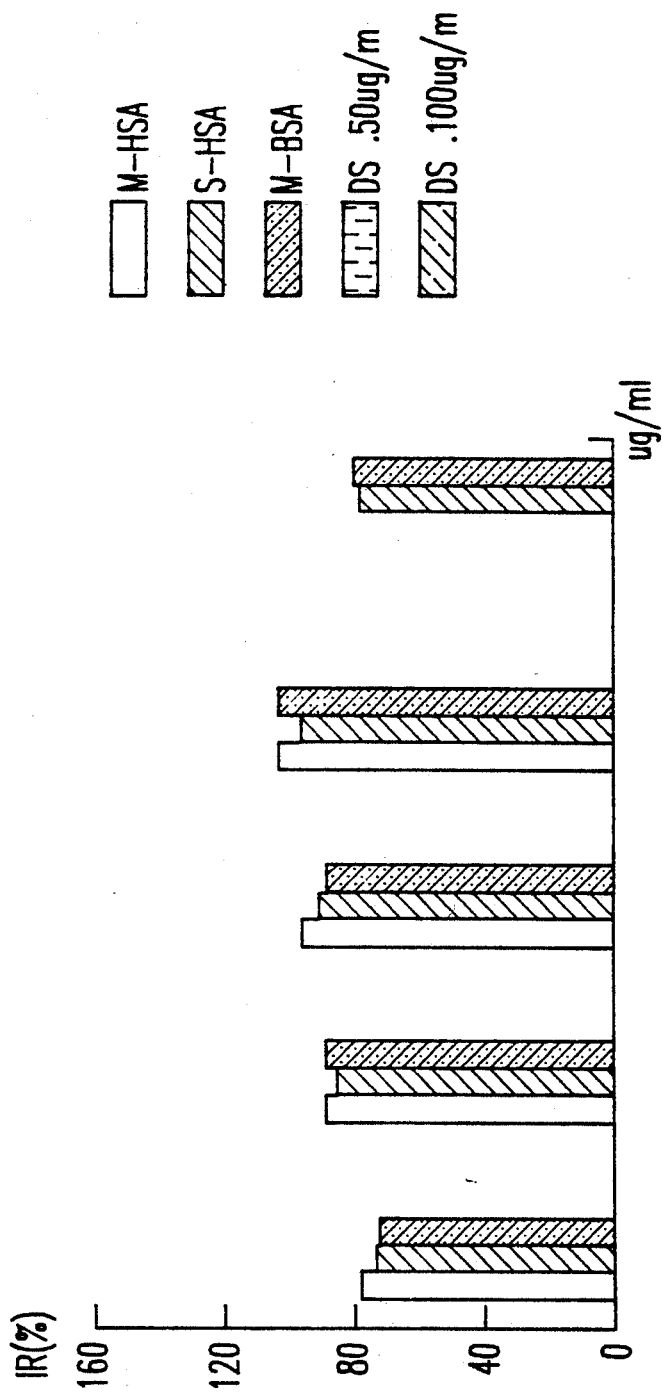
FIG. 3 is a graph showing the IRs for M-HSA, S-HSA, M-BSA, and DS at various concentrations in a culture broth wherein Molt-4/HIV and Molt-4 clone no. 8 were cultured in a mixture. The IRs were calculated from the measurement of the living cells by means of the MTT assay on the fourth day.

FIG. 3 is a graph showing the IRs for M-HSA, S-HSA, M-BSA, and DS at various concentrations (500 μg/ml, 100 μg/ml, 20 μg/ml, and 4 μg/ml for M-HSA, S-HSA, and M-BSA, and 100 μg/ml and 50 μg/ml for DS). Living cells were counted by means of the MTT assay.

As shown in FIG. 3, IRs for M-HSA were 102% at 500 μg/ml, 95% at 100 μg/ml, 88% at 20 μg/ml, and 77% at 4 μg/ml; IRs for S-HSA were 95% at 500 μg/ml, 89% at 100 μg/ml, 84% at 20 μg/ml, and 73% at 4 μg/ml; and IRs for M-BSA were 106% at 500 μg/ml, 87% at 100 μg/ml, 88% at 20 μg/ml, and 72% at 4 μg/ml. In the case of DS, on the other hand, IRs were 79% at 100 μg/ml and 78% at 50 μg/ml.

Figure 4:
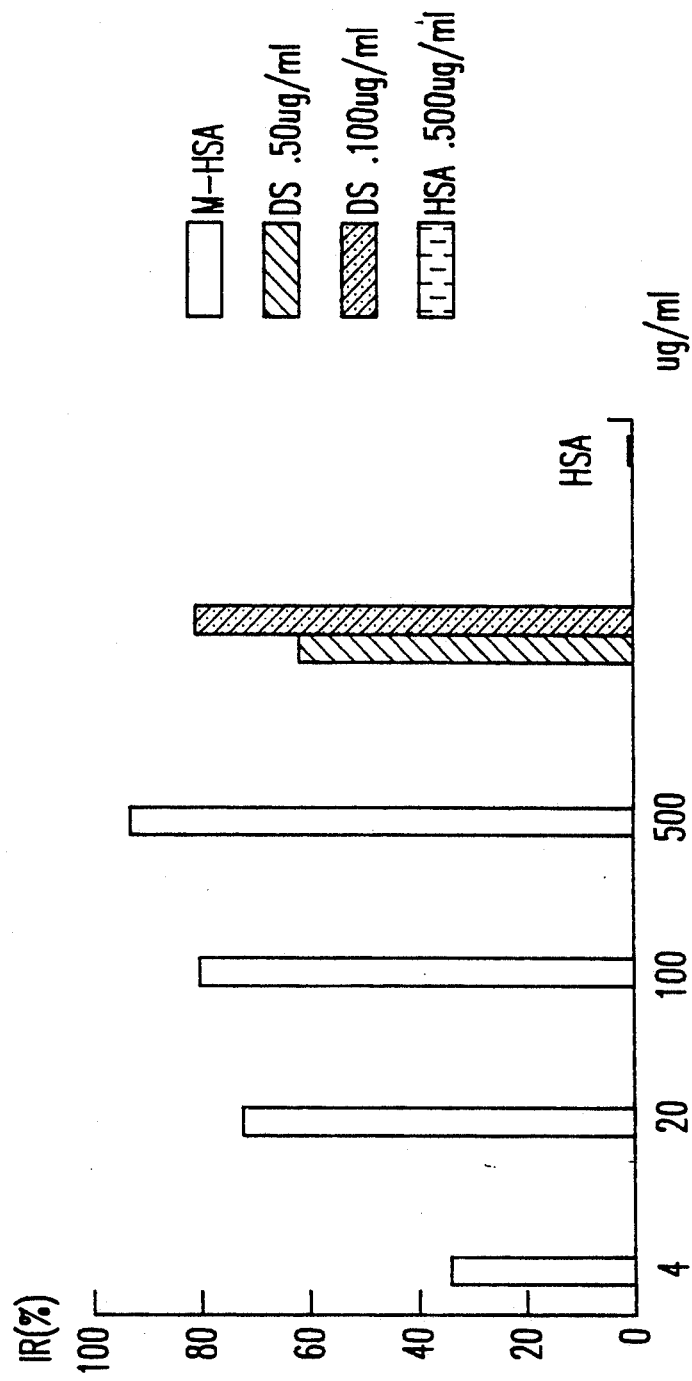
FIG. 4 is a graph showing the IRs for M-HSA, HSA, and DS at various concentrations in a culture broth wherein Molt-4/HIV and Molt-4 clone no. 8 were cultured in a mixture. The IRs were calculated from the measurement of the living cells by means of the Trypan blue color exclusion method on the fourth day.

FIG. 4 is a similar graph as that shown in FIG. 3, and was prepared to confirm the results of IRs obtained in the MTT assay in FIG. 3. In this experiment IRs for M-HSA (at concentrations of 500 μg/ml, 100 μg/ml, 20 μg/ml, and 4 μg/ml), HSA (at 500 μg/ml), and DS (at 100 μg/ml and 50 μg/ml), were calculated from the results of the assay on the fourth day by the Trypan blue color exclusion method. IRs for M-HSA were 91% at 500 μg/ml, 80% at 100 μg/ml, 75% at 20 μg/ml, and 35% at 4 μg/ml; IRs for DS were 84% at 100 μg/ml and 64% at 50 μg/ml. In contrast, a large cell denaturing or death inhibitive effect of HSA was hardly recognized even at the concentration of 500 μg/ml.

From the above experiments, M-HSA, S-HSA, M-BSA, and DS were recognized to exhibit a large cell denaturing or death inhibitive effect concentration-dependently. Also, M-HSA, S-HSA, and M-BSA were found to have a greater large cell denaturing or death inhibitive activity at a lower concentration; e.g. 20 μg/ml, than DS. In contrast, little large cell denaturing or death inhibitive effect was recognized with non-modified HSA.

EXAMPLE 2

(Inhibitive effect of other chemically modified plasma proteins on large cell formation in a mixed HIV infected cell-HIV non-infected cell culture system)

In order to demonstrate the anti-HIV effect of chemically modified plasma proteins other than chemically modified serum albumin of Example 1, experiments were carried out in which IRs were calculated based on the MTT assay and morphological observations were performed in the same manner as in Example 1 to evidence a large cell formation inhibitive effect in the mixed culture system of cell strains Molt-4/HIV and Molt-4 clone no. 8.

Test samples used were maleyl- or succinyl-modified plasma proteins, i.e., maleyl-modified immunoglobulin G (hereinafter referred to as M-Ig), succinyl-modified globulin (hereinafter referred to as S-Ig), maleyl-modified transferrin (hereinafter referred to as M-Tf), and succinyl-modified transferrin (hereinafter referred to as S-Tf), and succinyl-modified fibrinogen (hereinafter referred to as S-Fb). In addition, DS was used as a representative sample from known anti-HIV agents. These samples were added to Molt-4/HIV-Molt-4 clone no. 8 mixed culture systems in various concentrations to observe the inhibitory effect of the samples.

Figure 5:
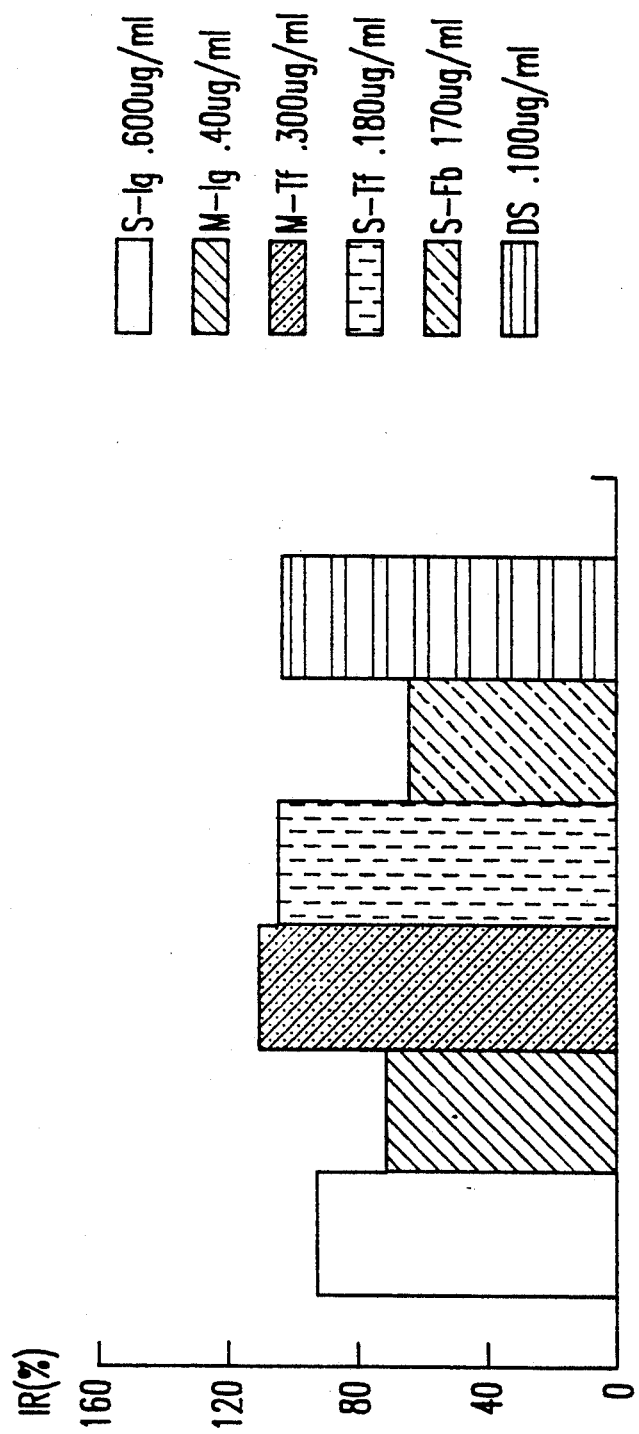
FIG. 5 is a graph showing the IRs for M-Ig, S-Ig, M-Tf, S-Tf, S-Fb, and DS at various concentrations in a culture broth wherein Molt-4/HIV and Molt-4 clone no. 8 were cultured in a mixture. The IRs were calculated from the measurement of the living cells by means of the MTT assay on the fourth day.
Figure 6A:
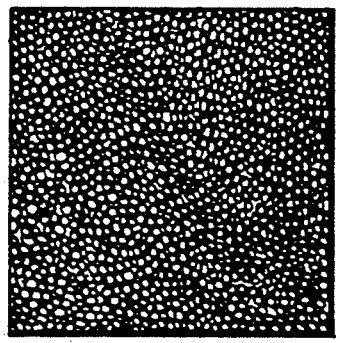
FIGS. 6(A) to 6(D) are sketches showing the microscopic morphological observations of the cells in direct T-cell (cell strain Molt-4 clone no. 8) infection systems with HIV in the presence of M-HSA or M-Tf on the fourth day of the culturing.
Figure 6C:
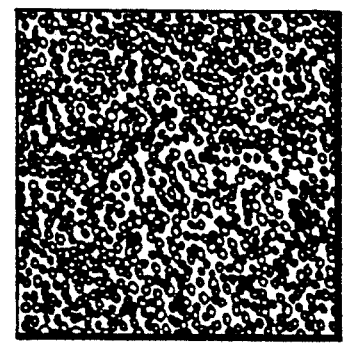
Figure 6B:
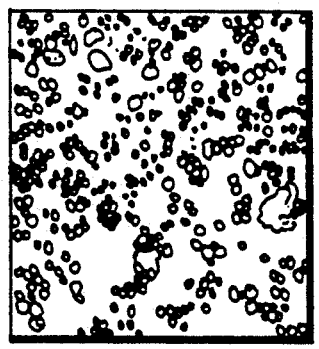
Figure 6D:
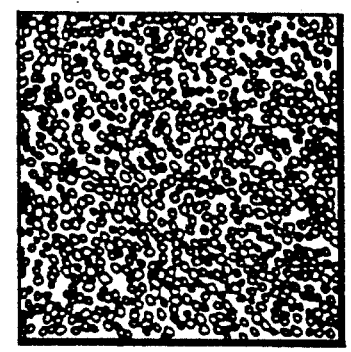

A 96-hole microplate was used for the mixed culturing of cell strains Molt-4/HIV and Molt-4 clone no. 8. The number of cells used and the culture conditions were the same as in Example 1. As controls, a system to which no anti-HIV agent was added and a system containing only Molt-4 clone no. 8 cell strain were cultured. The results are shown in FIG. 5. On the fourth day from the start of the culturing the MTT assay was performed and microscopic observation (magnification×100) was carried out on cell morphology.

FIG. 5 shows IRs of M-Ig, S-Ig, M-Tf, S-Tf, S-Fb, and DS at different concentrations, calculated from the number of cells which was determined by the MTT assay on the fourth day.

As indicated by FIG. 5, the IRs for M-IG was 70% at 40 μg/ml, for S-Ig was 91% at 600 μg/ml, for M-Tf was 110% at 300 μg/ml, for S-Tf was 104% at 180 μg/ml, for S-Fb was 65% at 170 μg/ml, and for DS was 103% at 100 μg/ml.

The above results provide evidences of a large cell denaturing or death inhibitive effect of maleyl- or succinyl-modified plasma proteins other than maleyl- or succinyl-modified albumin.

The morphological changes of the cells in the mixed culture broths, each containing the above test sample, were observed by microscopy to find the effect of the samples to prevent large cells from being produced (The results are not shown in figures).

Based on the results of Examples 1 and 2 various plasma proteins of which the polarity of the amino group of the amino acid residue is chemically modified with dicarboxylic anhydride are considered to effectively inhibit HIV infection.

EXAMPLE 3

(Inhibitive effect of maleyl- or succinyl-modified plasma proteins to inhibit disorders in Molt-4 clone no. 8 cells infected with HIV)

In Examples 1 and 2, an inhibitive effect of maleyl- or succinyl-modified plasma proteins was demonstrated with respect to the route of infection in which HIV infected cells bond with non-infected cells to agglomerate into large cells. In this example, experiments were conducted to show the inhibitive effect of maleyl- or succinyl-modified plasma proteins with respect to the other route of infection, i.e., the infection through the direct bonding of helper T-cells with HIV.

Test samples used were M-HSA, M-Tf, M-Ig, and S-Fb, and DS was used as a control. Molt-4 clone no. 8 strain was used as the helper T-cells with which HIV is to infect.

A solution containing HIV was prepared by culturing HIV producing cell strain Molt-4/HIV for 4 days, separating the supernatant from the culture broth by means of centrifugation, and subjecting the supernatant to filtration using 0.45 μm filter paper (manufactured by Millipore Co.).

The cell strain Molt-4 clone no. 8 was inoculated into a 96-hole microplate, $2.3 \times 10^4$ cells/150 μl culture liquid for each well. 50 μl of the HIV solution and the above mentioned test samples or DS were added to each well, and the culturing was carried out for 4 days. After completion of the culturing, microscopic morphological observation and measurement of the number of cells by means of the Trypan blue color exclusion method were performed.

FIGS. 6(A) to 6(D) show sketches of the microscopic (magnification: ×100) morphological observations of the cells. As is clear from these sketches, large, agglomerated cells which were denatured and died as a result of HIV infection were observed in the culture system of strain Molt-4 clone no. 8 to which only HIV was added [FIG. 6(B)], whereas the cells in the broth in which only Molt-4 clone no. 8 cell strain was cultured were alive [FIG. 6(A)]. In contrast, an HIV-induced large cell denaturing or death inhibiting effect was observed in the culture broth to which M-HSA [FIG. 6(C)] or M-Tf [FIG. 6(D)] was added.

Figure 7:
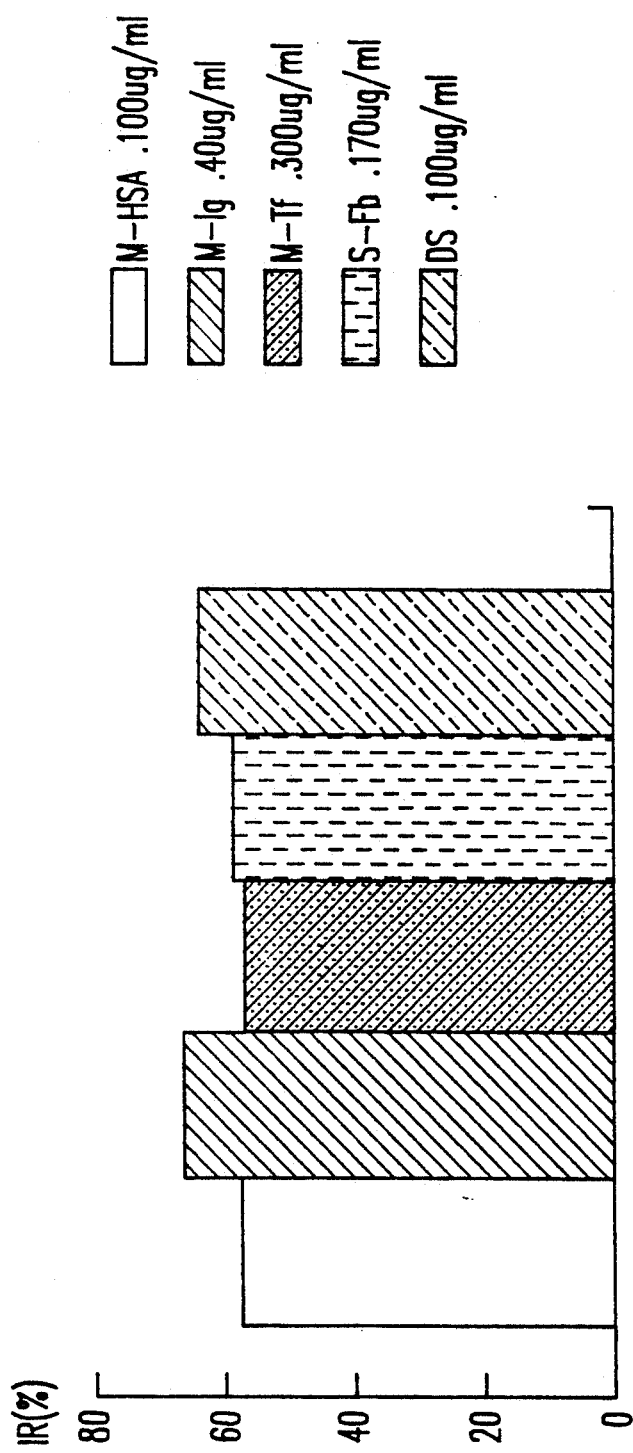
FIG. 7 is a graph showing IRs of M-HSA, M-Ig, M-Tf, S-Fb, and DS in direct T-cell (cell strain Molt-4 clone no. 8) infection systems with HIV on the fourth day of the culturing. IRs are calculated from the number of living cells measured by the Trypan blue method.

FIG. 7 is a graph showing the IRs calculated from the number of living cells which was measured by the Trypan blue method. IRs for M-HSA was 58% at 100 μg/ml, for M-Ig was 67% at 40 μg/ml, for M-Tf was 56% at 300 μg/ml, for S-Fb was 59% at 170 μg/ml, and for DS was 64% at 100 μg/ml.

The above results are considered to be evidence that maleyl- or succinyl-modified plasma proteins exhibited the inhibitive effect also in the direct infection of helper T-cells with HIV.

EXAMPLE 4

(Effect of maleyl- or succinyl-modified serum proteins on normal lymphocytes in an in vitro system)

DNA synthesis activity was measured using radioactive thymidine ($[^3H]$ Thymidine) as an in-take marker in order to investigate the effect of chemically modified HSA of this invention on normal human peripheral blood lymphocytes.

Lymphocytes were fractionated from normal human peripheral blood using Fycoll Pack (Farmacia Co.). The above-mentioned culture medium was added to the lymphocyte fractions. The lymphocytes were inoculated into a 96-hole microplate, $4.0 \times 10^5$ cells/200 μl culture medium per well.

An M-HSA, S-HSA, or HSA solution was then added to each of the microplate to a final concentration of 16 μg/ml, 32 μg/ml, 63 μg/ml, 125 μg/ml, 250 μg/ml, 500 μg/ml, 1,000 μg/ml, and 5,000 μg/ml, respectively. In order to compare the impact of chemically modified proteins to lymphocytes with the lymphocyte blastogenesis of mitogens, microplate systems were prepared in which was added, instead of the above test samples, phytohemagglutinin (hereinafter referred to as "PHA") to a final concentration of 5 μg/ml or concanavalin A (hereinafter referred to as "ConA") to a final concentration of 10 μg/ml. The cells were cultured in a humidified incubator (37° C.) in an atmosphere of air/$CO_2$ ratio of 95/5 for 60 hours. 0.5 μCi of radioactive thymidine (manufactured by Amersham Co.) was added to each well and the culturing was continued for another 12 hours. After completion of the culture, the cells were harvested onto glass fiber filter paper using a harvester. The filter paper was dried and the radio activity (unit: cpm) was measured using a liquid scintillation counter. Cells cultured by adding PBS instead of the test samples or mitogens were served as a control.

Figure 8A:
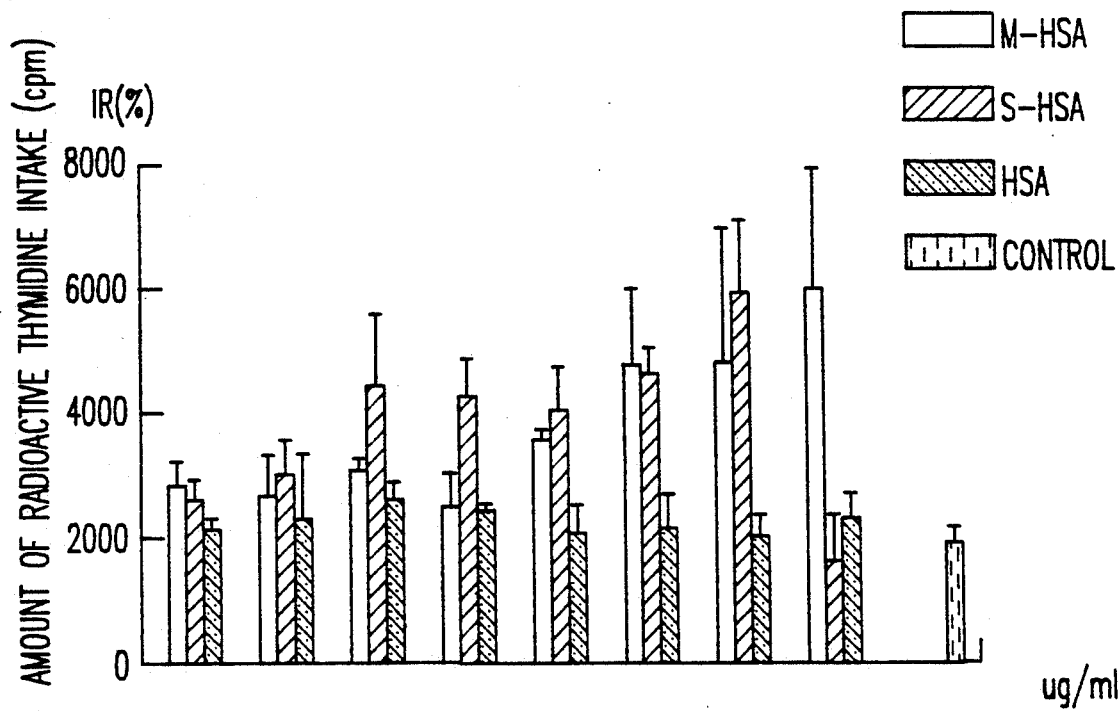
FIG. 8(A) is a graph showing the effect of maleyl- and succinyl-modified plasma proteins on normal lymphocytes in an in vivo system. The graph indicates the amounts of radioactive thymidine taken into the culture broths on the third day in which normal human peripheral blood lymphocytes were cultured in the presence of maleyl-modified human serum albumin, succinyl-modified human serum albumin, or non-modified human serum albumin.
Figure 8B:
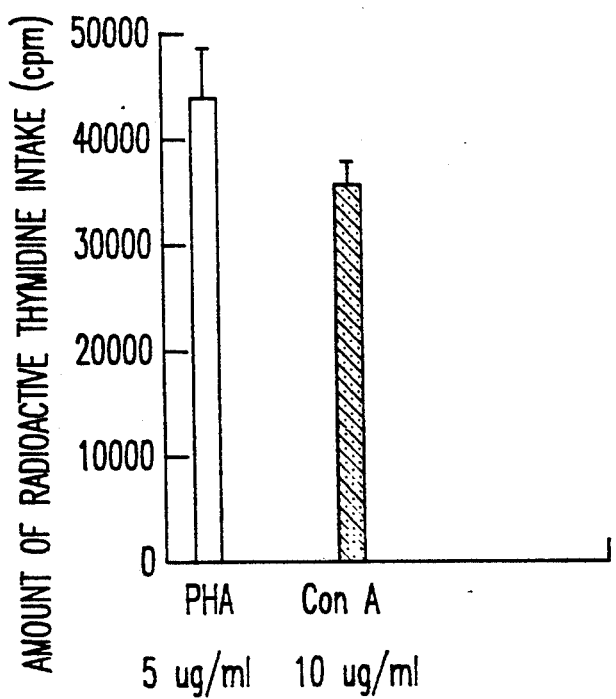
FIG. 8(B) is a graph showing the amounts of radioactive thymidine taken into the culture broths on the third day in which normal human peripheral blood lymphocytes were cultured in the presence of PHA or ConA.

The results are shown in FIGS. 8(A) and 8(B). In FIG. 8(A), it was demonstrated that there was some degree of DNA synthesis inhibitive effect by S-HSA at the concentration of 5,000 μg/ml, but no such effect by S-HSA at concentrations of 16–1,000 μg/ml. Both M-HSA and HSA exhibited no DNA synthesis inhibitive effect at concentrations of 16–5,000 μg/ml.

A slight lymphocyte blastogenesis was observed in the cells containing M-HSA. The degree was around 1/10 of the values for PHA or ConA which are shown in FIG. 8(B).

The above results showed no toxic nature of maleyl-modified HSA and succinyl-modified HSA to human lymphocytes during the interphase ($G_0$ phase) of the cell cycle.

EXAMPLE 5

(Acute toxicity test)

Acute toxicity test of the chemically modified plasma proteins of this invention was carried out by intravenous injection of M-HSA to mice.

As M-HSA was considered to be a low toxic material, the technically allowable maximum amount of M-HSA, 3.92 g/kg, was administered in this test.

Specifically, 3.92 g/kg of M-HSA was intravenously administered to each of 5 DBA/2 male mice (provided by Japan Charles River Co., Ltd.) weighing 24.4 to 28.9 g, and general conditions and changes in body weight of the mice were observed. As a result, no abnormality was observed.

It is supposed that the same results will be obtained from any products produced by maleyl- or succinyl modification of plasma proteins, and that all maleyl-modified plasma proteins as well as succinyl-modified plasma proteins are safe.

INDUSTRIAL APPLICATION OF THE INVENTION

As evident from Examples 1–5, plasma proteins modified with dicarboxylic anhydride, which are the effective components of the anti-HIV agent of this invention, inhibit the formation of large cells in mixed culturing of HIV infected cells and non-infected cells as well as the direct infection of helper T cells with HIV. They do not have any influence on DNA synthesis even at a high concentration. Also, they are considered as very safe materials due to the fact that they exhibited no abnormality in acute toxicity tests.

From the above results plasma proteins modified with a dicarboxylic anhydride are expected to be applicable to the treatment of HIV infected patients.

What is claimed is:

1. A composition for inhibiting large cell formation comprising an effective amount of a plasma protein in which the polarity of an amino group of an amino acid residue constituting the plasma protein is chemically modified into a negative moiety and a pharmaceutically acceptable carrier.

2. The composition of claim 1, wherein said amino group of an amino acid residue is modified by a dicarboxylic anhydride.

3. The composition according to claim 2, wherein said dicarboxylic anahydride is maleic anahydride or succinic anhydride.

4. The composition according to claim 1, wherein said plasma protein is a member selected from the group consisting of human serum albumin, human immunoglobulin, human transferrin, human fibrinogen and bovine serum albumin.

* * * * *

UNITED STATES PATENT AND TRADEMARK OFFICE
CERTIFICATE OF CORRECTION

PATENT NO. : 5,256,412
DATED : October 26, 1993
INVENTOR(S) : Hajime Tsunoo, et. al.

It is certified that error appears in the above-indentified patent and that said Letters Patent is hereby corrected as shown below:

Column 11, line 5, "dicarboxylic anahydride is maleic anahydride" should read --dicarboxylic anhydride is maleic anhydride--.

Signed and Sealed this

Twentieth Day of September, 1994

Attest:

BRUCE LEHMAN

*Attesting Officer*   *Commissioner of Patents and Trademarks*